July 18, 1933. R. DIENER Plant Pat. 70
ROSE
Filed June 6, 1932
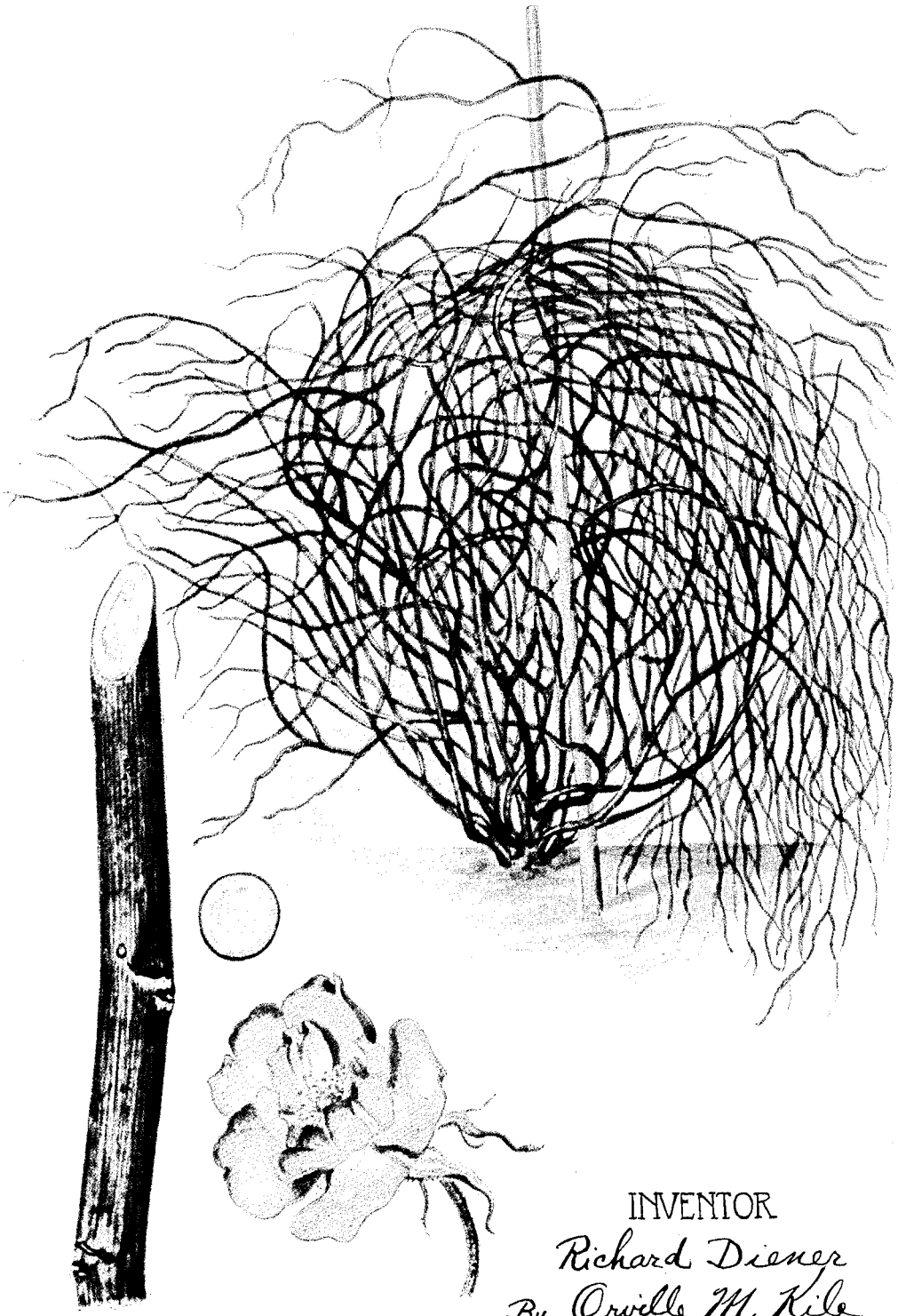
INVENTOR
Richard Diener
By Orville M. Kile
PLANT PATENT AGENT Patented July 18, 1933

Plant Pat. 70

UNITED STATES PATENT OFFICE

RICHARD DIENER, OF OXNARD, CALIFORNIA

ROSE

Application filed June 6, 1932. Serial No. 615,741.

My invention relates to improvements in trailing or climbing rose plants suitable for the production of grafting understock, standard roses, and for other purposes. The object of my invention is to provide a new and distinct variety of rose plant or bush of the type mentioned, exceptionally free from disease, readily propagated, and having the habit of producing extraordinary amounts of wood in a single season of growth. Such a rose plant is much desired as the understock or base for the production of grafted roses. When the additional quality of a smooth, green, thornless cane is added, as is the case in the present invention, the wood is valuable for the production of tree or standard roses. No superior quality is claimed for the blossoms.

My new variety originated as the result of a cross between the German rose "Veilchenblau"—or in English "Violet Blue"—and a blue sport of the Veilchenblau. After making this successful cross and experimenting with the growing and grafting qualities of this variety for several years, I began to use wood of this variety in the production of grafted roses on my own premises but the variety has not, to date, been offered for sale.

The accompanying illustrations show (1) a single year's growth on a three year old root, (2) a six-inch section of a cane, (3) a cross section of a cane, and (4) a blossom in an advanced stage of maturity.

The following is a detailed description of the principal features of this rose plant and the flowers produced by same:

The plant shown in the illustration represents the growth in a single full Southern California season, out of doors. The root is three years old but all the growth shown was made in one season, since the growth the second year had been cut off just above the ground at the end of the season. The illustration was made at a season when the foliage had fallen off. The main mass of the bush here shown is about 4 feet high and the individual canes shown reach a length of 8 to 10 feet. The canes taper so slightly that sections four feet long, cut six inches above the ground show no appreciable differences in diameter at the two ends.

The surface of the canes is almost smooth and of a light green color, with a brownish overlay at points. The leaf scars occur about two inches apart on the mature canes. The core or pith area is relatively small, thus producing a strong cane. The wood is almost entirely free from thorns; only occasionally is a thorn found.

So adaptable is this rose wood to use as understock, that I have found that varieties of roses which on ordinary understock can be grafted only with the greatest difficulty, will make vigorous growth when grafted on this new understock.

Its superior rooting and grafting qualities are also shown by the fact that I cut 4-foot shoots or canes from this variety in the fall, successfully root them during the winter and then graft tops on in the spring, thus producing in a single year tree or standard roses which with other understock would require two or three years to produce equivalent results.

Short cuttings of cane, potted in the fall will make an abundant growth of roots and be ready for grafting for greenhouse forcing purposes the following spring.

This new variety appears to be free from attacks of mildew, none ever having been seen during the five or more years this plant has been under observation.

*Foliage.*—The leaves are borne seven to a leaf-branch on the mature branches, with the number reduced to five and to three in the immature stages. The central stem of each leaf branch bears one to many rather prominent spines or thorns. The individual leaves are of typical rose shape, though small—about 1¾ inch long by 1 inch wide—and the leaf edges are rather deeply notched.

*Stipules.*—Relatively wide, with straight pointed ends, and having irregular hairy edges.

*Buds.*—When tightly closed are long and tassel-like, the extra length being due to the length of the sepals rather than to the size of the petals.

The flowers are single, ordinarily having 10 petals. The flowers average 2 inches or more across the top when fully expanded. Borne in clusters made up of three to five groups of three buds or flowers each, with an additional first-blooming flower at the end of the branch bearing the cluster. The peduncle of this terminal flower is 1¾ to 2 inches long but the peduncles of the rest of the buds and flowers composing the cluster are somewhat shorter. All the peduncles are closely beset with small spines or coarse hairs. A reddish-brown color covers not only the peduncles and the spines but portions of the buds as well.

The dominant color of the fresh cut flower is "rose red" as shown in Plate XII of Ridgeway's Color Standards and Nomenclature. The lighter shades are "spinel red" (Plate XXVI). As the flower ages the purple shades appear as indicated in the illustration which shows a flower cut about three days but kept moist in the interval and freshened by immersion in water. The lighter purples shown are approximately "rose purple" (Plate XXVI) and the dark shades shown are approximately "phlox purple" (Plate XI). The five petals constituting the inner whorl each has a white, somewhat irregular stripe running vertically down the petal from top to base.

The hips are large in proportion to the size of the flower, and somewhat globular or bulbous in shape.

An abundance of long yellowish stamens and pistils is produced in each flower. The anthers are yellowish brown.

The sepals are five in number, each about ¾ inch long, and taper sharply to a point. One or two sepals on a flower may be slightly branched but do not tend toward the foliaceous form.

The more important features which I believe distinguish my new variety of climbing or trailing rose from all other known varieties are:

First, the extreme growth of long canes in a single season.

Second, the ease with which cuttings of the canes take root and the large amount of roots produced in a short time.

Third, the ease with which grafts or buds will grow when this variety is used as an understock.

Fourth, the smoothness of canes and almost complete absence of thorns.

Fifth, the freedom from plant diseases.

Sixth, the distinctive character of buds and flowers produced.

What I claim as new is:

The climbing or trailing rose plant herein described and shown, characterized particularly by its extraordinary growth of wood, the ease with which cuttings take root, and its superior grafting qualities, all of which make it particularly suited for use as understock.

RICHARD DIENER.